United States Patent [19]
Lazeration

[11] Patent Number: 5,113,688
[45] Date of Patent: May 19, 1992

[54] LABORATORY TRACTION TEST

[75] Inventor: Joel J. Lazeration, Akron, Ohio

[73] Assignee: The Goodyear Tire & Rubber Company, Akron, Ohio

[21] Appl. No.: 671,557

[22] Filed: Mar. 19, 1991

[51] Int. Cl.⁵ .................................. G01N 19/02
[52] U.S. Cl. .................................. 73/8; 73/9; 73/146
[58] Field of Search .................. 73/9, 7, 8, 146, 847, 73/865.6

[56] References Cited

U.S. PATENT DOCUMENTS

| | | | |
|---|---|---|---|
| 1,327,838 | 1/1920 | Naylor | 73/9 |
| 1,490,603 | 4/1924 | Elverson | 73/9 |
| 2,058,805 | 10/1936 | Lee | 73/9 |
| 3,638,230 | 1/1972 | Umeno et al. | 73/843 |
| 3,982,427 | 9/1976 | Decker | 73/815 |
| 4,275,600 | 6/1981 | Turner et al. | 346/33 R |

Primary Examiner—Donald O. Woodiel
Attorney, Agent, or Firm—David E. Wheeler

[57] ABSTRACT

A method and apparatus for predicting tire traction characteristics of tread compounds are provided. The method makes possible the determination of such characteristics without building tires. Also, the compounds can be easily characterized for a large number of different road surfaces and many different weather conditions. In the method, about 2 to 10 gms of tread compound is molded into a sample which can be tested for traction on the apparatus. Peak traction, slide traction and other traction characteristics of the compound can be correlated with traction properties of known compounds, thereby establishing the expected traction properties of the test compound in a tire.

13 Claims, 8 Drawing Sheets

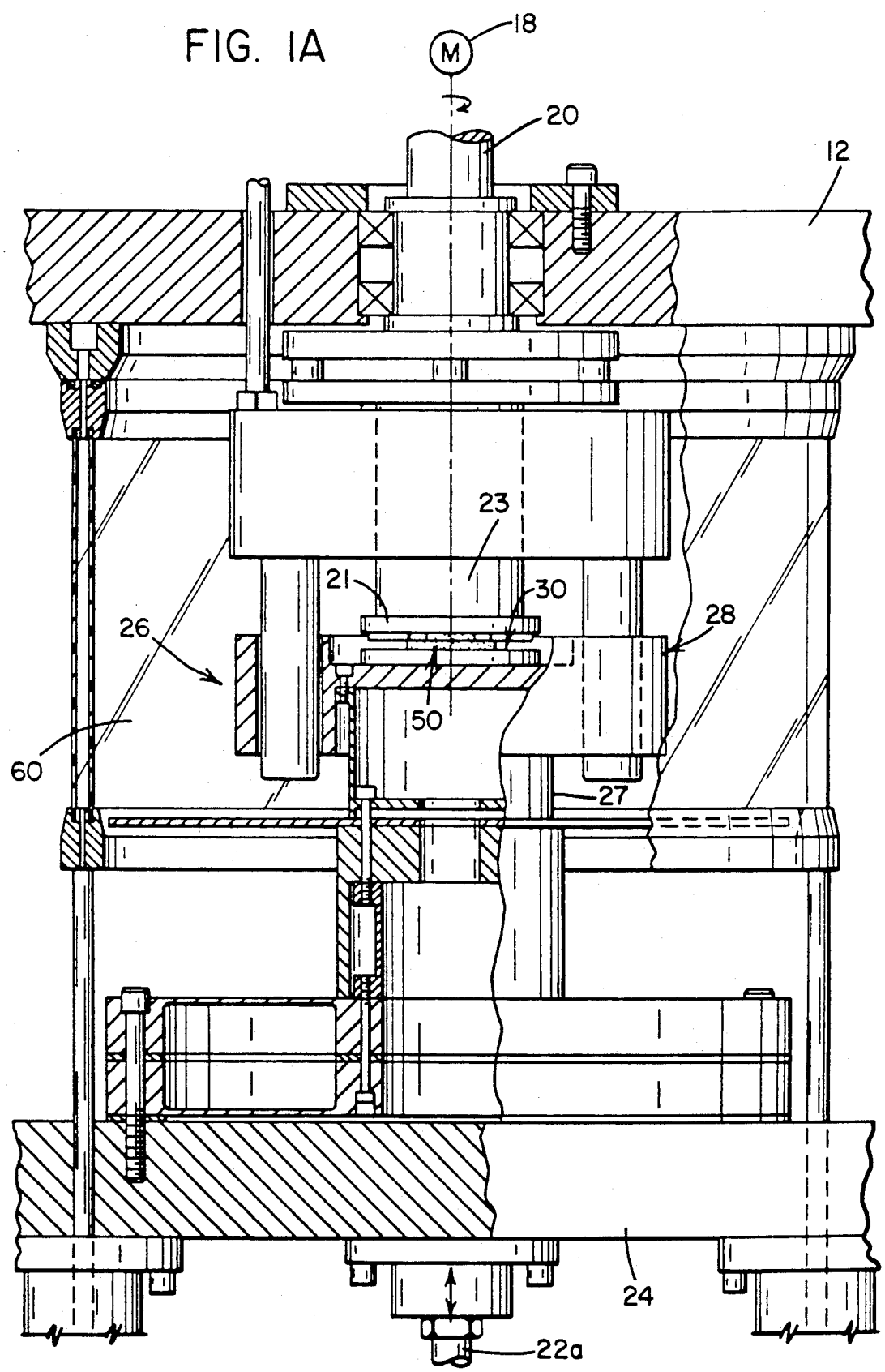
FIG. IA 5,113,688

LABORATORY TRACTION TEST

BACKGROUND OF THE INVENTION

The present invention relates to a method and apparatus for predicting tire traction characteristics of tread compounds.

Although compounders can predict, to a certain extent, the properties of specific rubber compounds, the properties ultimately can only be determined by testing. In the past, when the compound was a tread compound, traction properties could only be determined by building a tire and subjecting the tire to various traction tests.

Since tire building is very time consuming and expensive, especially in small lots, in the past, traction testing only served to determine if the properties were within acceptable ranges for given conditions. It was very difficult to fully optimize a tread compound to optimize traction properties.

There are known in the art a number of tests for measuring the friction properties of rubber. Friction properties, however, do not correlate well with traction properties because of the rate and frequency of deformation (depending on the speed of a rubber sample and the number of asperities on the traction surface) components of traction.

It is an object of the present invention to provide a method and apparatus for using very small samples of tread compounds to determine the traction characteristics of the compounds. Since small samples of the tread compound are used for testing, and it is not necessary to build a tire, traction characteristics can be determined very quickly and inexpensively. Since the tread compounds can be made in small batches, a large number of compounds can be made for screening, to determine which compound has the best properties. Also, since the testing surface in the apparatus may be changed to represent a large number of different road surfaces and different conditions, the traction properties of the compounds may be observed to determine which compound has the best traction on a specific road surface under specific conditions.

Other objects of the invention will become apparent from the following description and claims.

SUMMARY OF THE INVENTION

A method of predicting tire traction characteristics of tread compounds is provided. The method comprises preparing a sample of tread compound in a form suitable for traction testing and placing the sample in a testing apparatus opposite a testing surface, said apparatus being capable of causing a rotating relationship between the sample and the test surface and measuring the torque therebetween. When the sample is contacted with the test surface and the apparatus initiates the rotating relationship, the peak torque is measured and a torque v. time curve (slide traction curve) is established for the sample. The torque v. time curve is then correlated with established curves for desired traction characteristics. In preferred embodiments, the testing surface may be prepared to have characteristics that resemble a particular road surface, and the pressure, speed and temperature of the sample and the test surface may be precisely controlled. The apparatus may also be adapted to provide for wet testing of the sample to simulate wet road conditions.

Also provided is an apparatus for predicting tire traction characteristics of tread compounds. The apparatus comprises a frame comprising a horizontally disposed base and a horizontally disposed top, each having an upward side and a downward side, the top and base being connected by vertically disposed guiderails. A motor is associated with the top having its driveshaft oriented vertically downward on the downward side of the top. A sample mount is attached to the drive shaft of the motor. On the upward side of the base, a loading cylinder is provided which contacts a movable plate which engages the guide rails. A load cell is provided on the upper surface of the movable plate in vertical alignment with the sample mount. A test cell, adapted to hold a fluid, is associated with the load cell, and the base of the test cell comprises a test surface which is designed to demonstrate the properties of a road surface. The loading cylinder is adapted to move the movable plate on the guide rails to bring the test cell into contact with a sample in the sample mount. In a preferred embodiment, the apparatus is equipped with a chamber on the movable plate which movably engages sealing means on the top to provide means for controlling the environment around the sample mount.

Also provided is a testing surface which is made of a wear resistant material which is made to have surface characteristics which resemble a particular road surface.

BRIEF DESCRIPTION OF THE DRAWINGS

FIG. 1A illustrates the testing portion of the apparatus of the invention.

DETAILED DESCRIPTION OF THE INVENTION

Rotational friction testing of hardened surfaces is known in the art for evaluating the wear properties of, for example, ceramic engine parts. A machine manufactured specifically for rotational friction testing (Tribology) is available from Advanced Mechanical Technology Inc.(AMTI), Newton, Mass. In accordance with the present invention, a rotational friction testing apparatus from AMTI has been modified to hold a rubber sample parallel (within ±0.01°) and in concentricity (±0.0005 in.) relative to a testing surface, and to provide a temperature range of −100° to 300° F., a rotational speed of 700 rpm, a load of 0-200 pounds, and to measure torque up to 200 inch pounds.

Figure 1:
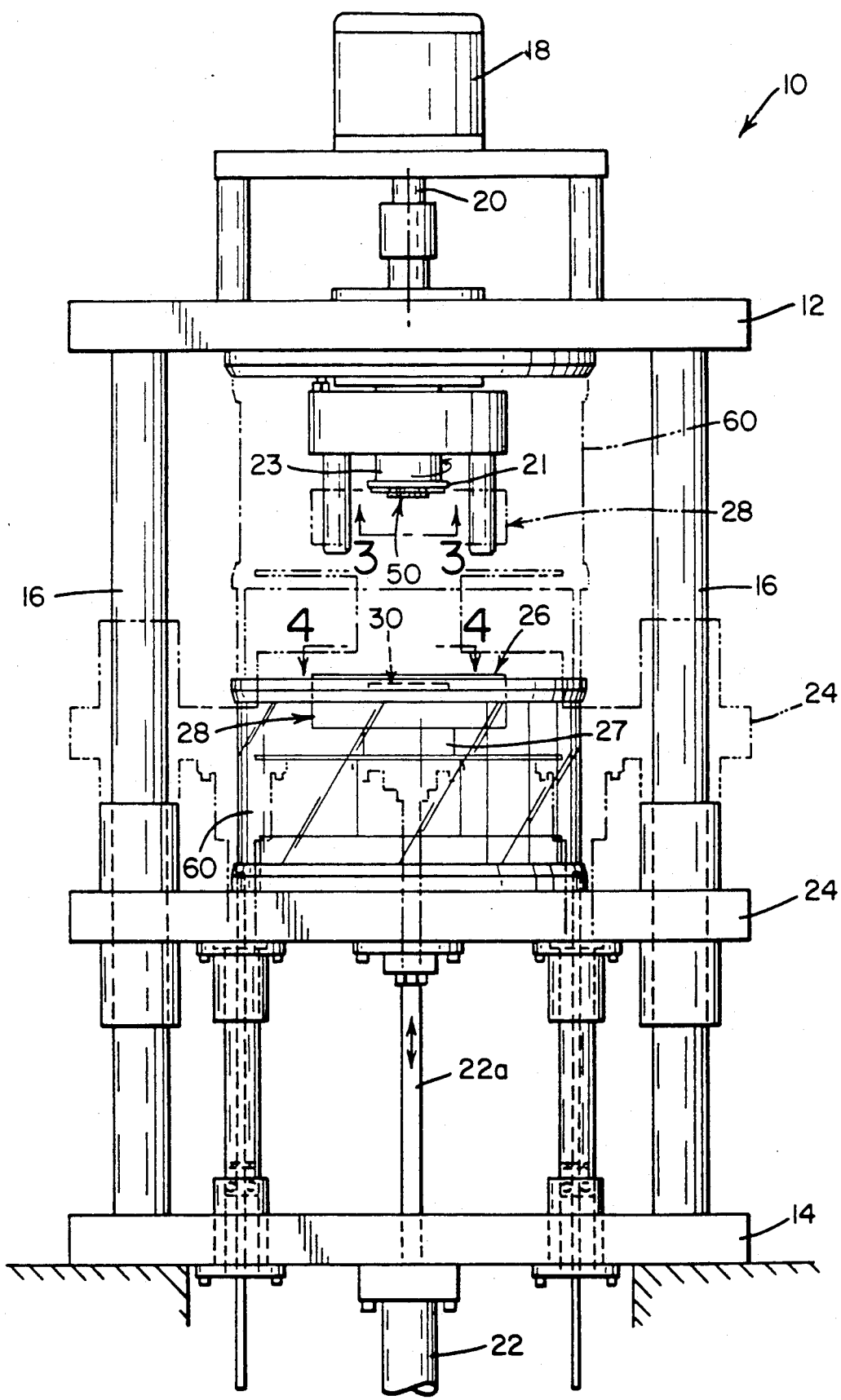
FIG. 1 illustrates a partial cross section view of the major movable parts of the apparatus.

With reference now to FIGS. 1 and 1A, an illustrated embodiment of the apparatus 10 of the invention comprises a top plate 12, a base plate 14, and vertical guide bars 16 connecting top 12 and base 14. A spindle motor 18 is mounted to top 12 with its drive shaft 20 oriented vertically downward. A sample mount 21 is associated with drive shaft 20 at the terminus 23 thereof for holding a sample 50. A loading means 22 (which optionally may comprise a hydraulic piston) is mounted on base 14. A movable plate 24 is associated with loading cylinder 22. Movable plate 24 engages vertical guide bars 16 and is slidable thereon. A loading cell 26 having torque measuring means 27 associated therewith is mounted on the upward side of movable plate 24 substantially in vertical alignment with drive shaft 20. A test cell 28, having a testing surface 30 comprises part of load cell 26 in alignment with sample mount 21.

Environmental chamber 60 is made of LEXAN®, and permits viewing of the test sample as well as environmental control. A separate cooling and heating units provide temperature control of the test surface. In the illustrated embodiment drive screw 22a is used to load the sample, although those skilled in the art will recognize that other loading means can be used. The apparatus was modified to use the largest servo possible for apparatus of this size.

Those skilled in the art will recognize that other arrangements of apparatus 10 may be possible without changing its operation. For example, motor 18 may be mounted above or below top 12. Also, load cell 26 may comprise, in addition to test cell 28, nothing more than welds for attaching test cell 28 to movable plate 24 and the torque measuring means may be located elsewhere on the apparatus. Other possible modifications of the apparatus will be apparent to those skilled in the art.

Figure 2:
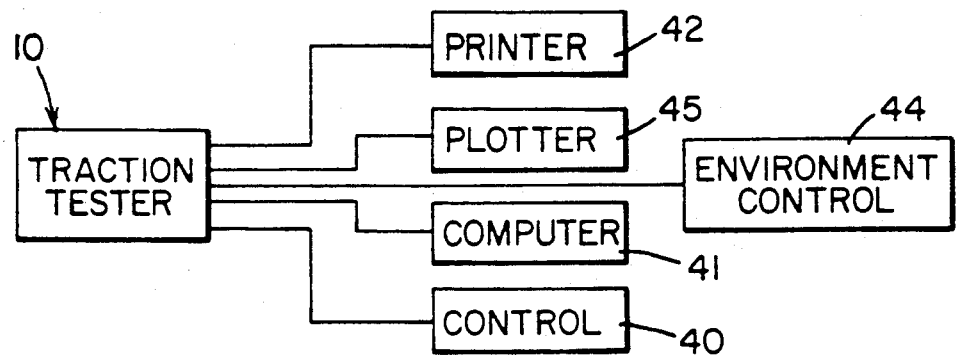
FIG. 2 is a schematic illustrating various components of the apparatus of the invention.

With reference now to FIG. 2, the sample handling portion 10 of the apparatus may be connected to a control panel 40, computer 41, printer 42, environment control system 44, and other data acquisition and display systems. Control panel 40 may be used to manually control the pressure, temperature and speed of rotation between sample 50 and testing surface 30, or computer 41 may be used to program these parameters to provide a specific sequence of parameter changes. For example, using computer control, the apparatus can be programmed to test a sample at −20° F., under a load of 100 psi, at a speed of 20 rpm for 3 seconds, reverse the direction of rotation for 3 seconds at 10 rpm, and provide data on the torque measured at each point in the operation in digital form. The output, i.e. the torque measured by the apparatus can be provided in analog form. The results measured by torque measuring means 27 may be fed into printer 42 to give results digitally. (Analog Torque output must first go through an A/D converter. Digital results can then be fed to a computer for processing.) Optionally, the results may be fed to a plotter 45 to provide a conventional traction curve showing peak torque and the slide traction curve.

Figure 3:
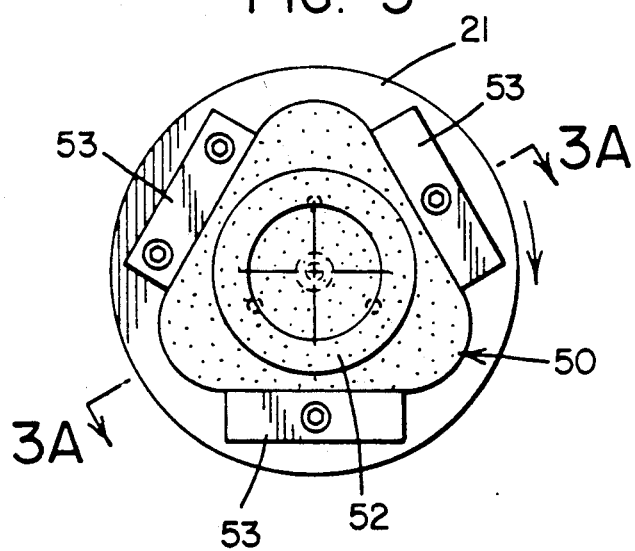
FIG. 3 illustrates a test sample having an annular testing surface mounted in the apparatus.
Figure 3A:
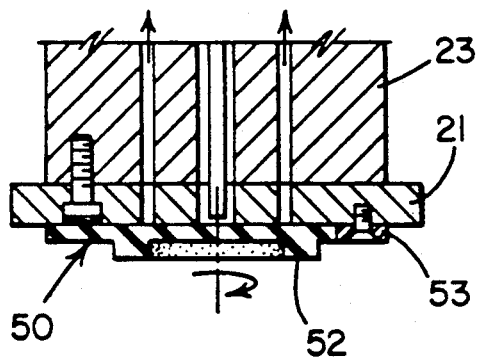
FIG. 3A is a cross section view taken along line 3A in FIG. 3.
Figure 3B:
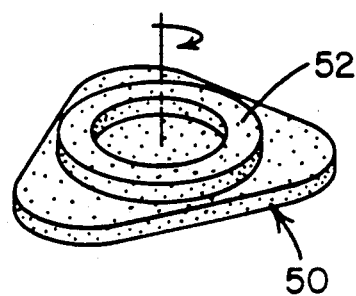
FIG. 3B is a perspective view of the test sample.

In the illustrated embodiment, sample 50 is held in place by vacuum in order to provide a quick change method of changing the sample. Accordingly, in the illustrated embodiment, the sample 50 (FIGS. 3, 3A and 3B) comprises a single molded piece of rubber having a shape and size suitable for snap-in placement and quick removal of the sample. Brackets on hooks 53 on the sample mount, and the shape of the sample, keep the sample from slipping in the sample holder during the test. Only about 2 to 10 gms of tread compound are needed to mold the sample. After the desired load is obtained, the test sample is set in motion by conventional means, for example a dynamic clutch, and the torque is measured using a strain gauge.

When smooth rubber is statically contacted with a smooth surface, the predominant property of rubber is adhesion. When pressed against a smooth surface, rubber forms a suction grip that is so strong it sometimes has to be broken loose. This property, to a large extent is the basis for the prior art rubber friction test.

In the illustrated embodiment, in order to assure the proper slip properties of the sample, the sample is molded with annular ring 52 for contacting testing surface 30. Those skilled in the art will recognize that other configurations of the test sample are possible which will provide the desired traction curve. Those skilled in the art will also recognize that once a significant number of tread compound samples have been characterized on the testing apparatus, and the results have been correlated with traction results achieved by tires, use of the traction curve may not be necessary to obtain meaningful results.

There is a need to precisely define the test surface because of the tractional characteristics of rubber. Rubber traction has both adhesional and deformational components, but for wet and/or dirty roads it is the deformational component that dominates the coefficient of traction. Therefore, asperity size will determine the amount of deformation the rubber will undergo. It will also determine the local contact pressures because net contact area is much less than the area of the rubber specimen. Asperity distribution on the test surface combined with the rotational speed of the apparatus, determines the frequency of deformation. Because rubber is viscoelastic, it is apparently important that the rates of deformation and magnitudes of deformation of the tread lug on the road match the deformation and magnitude of deformation of the test sample on the test surface in the lab.

Figure 4:
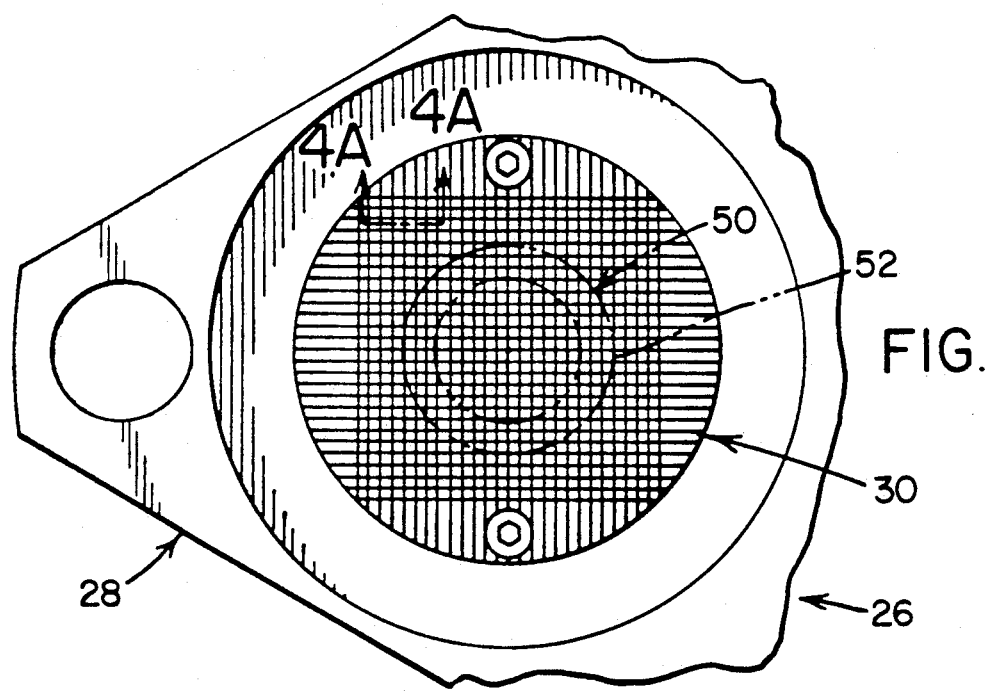
FIGS. 4, 4A and 4B illustrate a testing surface used in the apparatus.
Figure 4A:
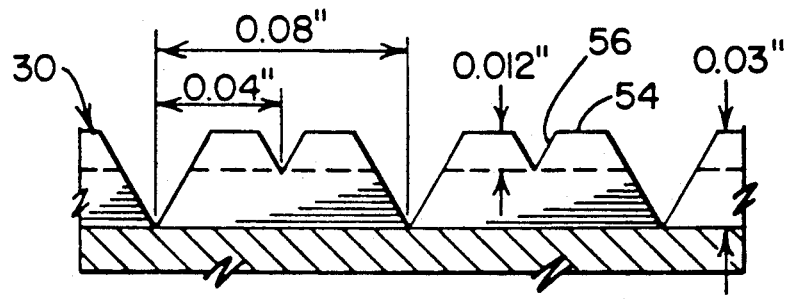
Figure 4B:
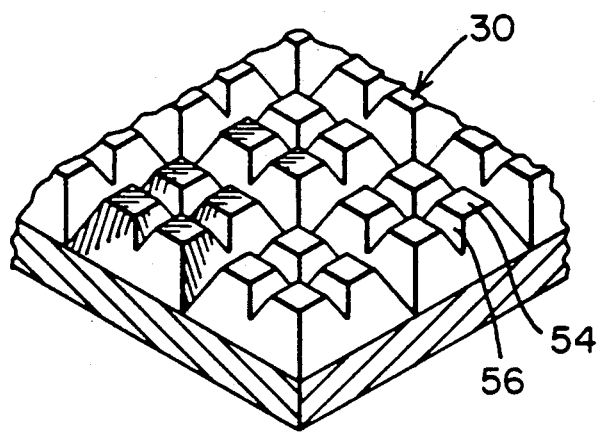

With reference now to FIGS. 4, 4A, and 4B, in the illustrated embodiment, testing surface 30 comprises a number of asperities 54 that are designed to duplicate, in properties, the asperities of a road surface. To measure the traction of a particular tread compound with respect to a particular type of road surface, the testing surface can be changed to match the properties of the road surface of interest. With regard to the frequency of asperities, their depth, and the angle of their side walls 56.

To construct a test surface to simulate a given road, a profilometer would be used to profile the surface of the road. From the profile, a mean or (rms) root means square asperity size and depth can be found and then these can be scaled down for the test surface. Once these parameters are known, a rotational speed for the test can be calculated to match the frequency of the road traction test.

Originally, it was believed that a test surface made of the same material as the road surface would give the best correlation in testing results. Concrete and asphalt, however, tend to wear quickly under test conditions, and a more durable test surface is required. It is desirable, however, that the test surface has a texture or roughness (asperities) which provides properties under test conditions that resemble or duplicate the properties of concrete or asphalt or other road surface. This is important since the ranking of the test compounds (as to the best traction properties) is dependent, among other things, on the test surface parameters such as the size and frequency of asperities. The availability of a number of test surfaces provides the technician with the ability to test a particular tread compound for potentially all known road surfaces.

In the illustrated embodiment, the testing surface is substantially flat, but as discussed above, those skilled in the art will be able to devise other surface types after a sufficient number of compounds have been characterized to correlate compound traction properties to tire traction properties.

In the illustrated embodiment, the testing surface is made of hardened 4142 tool steel. Those skilled in the art will recognize that other metals, certain ceramics, glass and other similar materials can also be used.

With reference again to FIG. 1A, the apparatus 10 may be equipped with environmental chamber 60 which is adapted to enclose the sample and testing surface to control the environment of the sample during testing.

In the illustrated embodiment, chamber 60 is adapted to move with moving plate 24 to engage a sealing means associated with top 12. Those skilled in the art will recognize that any suitable sealing means can be used.

Using environmental chamber 60, it is possible to test rubber traction in a wide range of temperature and humidity conditions. In the illustrated embodiment, the apparatus is adapted to test rubber samples at $-100°$ F. to $400°$ F., under humidity conditions of 0% to 100%. This, together with the ability to change the testing surface, makes it possible to determine which tread compound, of a large number of tread rubber compounds, has the best properties for a particular road surface and particular weather conditions.

Wet traction testing is of particular interest since wet traction data is considered most important in the GM Traction Test. Also, using a wet sample and test surfaces reduces the possibility of obtaining skewed test results because of dust or other contamination.

The test cell 28 is adapted to hold a fluid, especially water, for wet traction testing. For wet traction testing, the test cell is filled with water to a specified depth, and the sample is contacted with the testing surface in the usual manner. The water in the test cell can also be frozen for ice testing.

Figure 5:
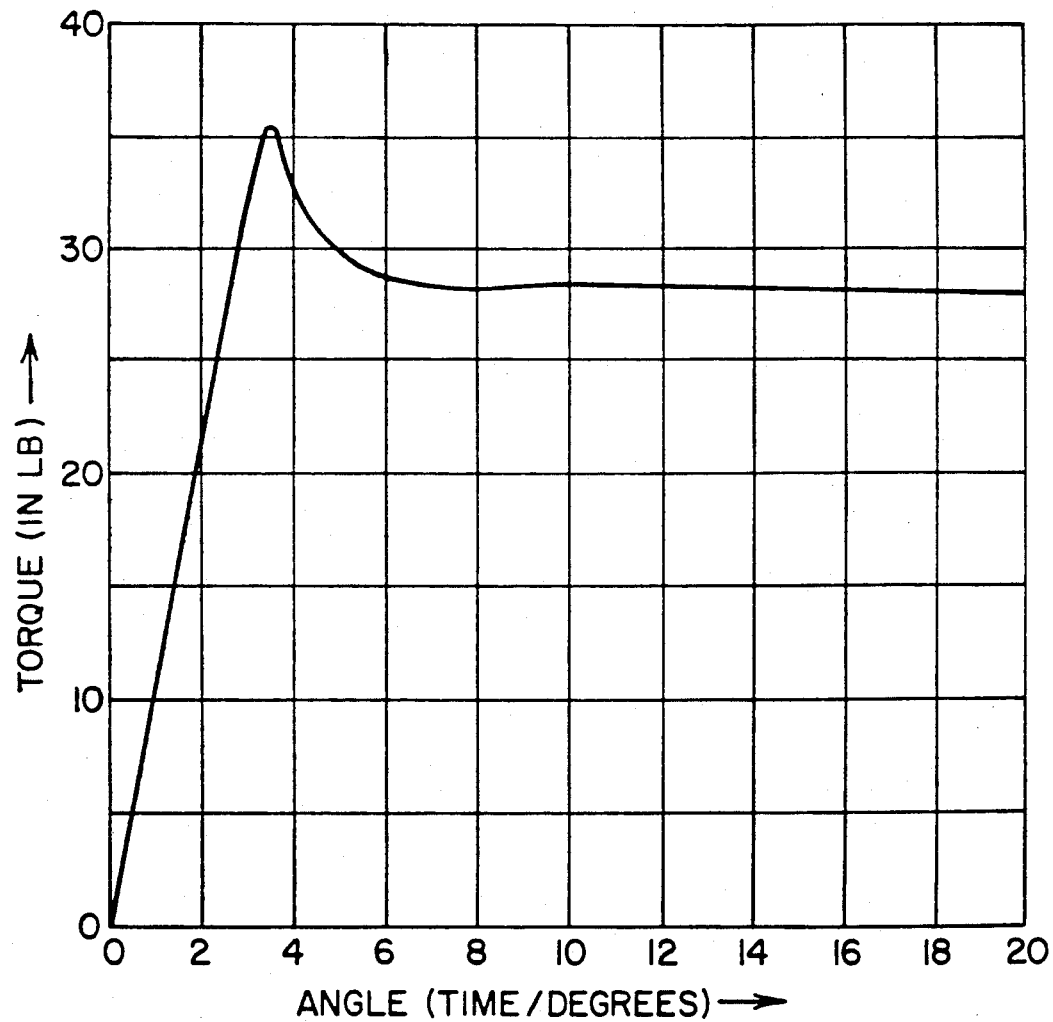
FIG. 5 illustrates a traction curve developed by the apparatus.

With reference now to FIG. 5, a typical traction curve of a rubber sample, produced by the apparatus of the invention, is illustrated. Those skilled in the art will recognize that the traction curve of the rubber sample is substantially the same as the traction curve obtained when testing tire traction.

The traction curve measures torque v. time or torque v. angular velocity. When a sample is contacted with the testing surface and rotated, the sample applies a torque to the testing surface, when the initial torque is overcome as the sample continues to rotate, the sample starts to slide but still applies resistance to the testing surface because of the grip or traction between the rubber and the testing surface. The maximum torque measured before the sample slips is known as the peak torque, and the torque measured during slide or slipping of the sample is known as the slide curve.

The apparatus of the invention easily duplicates the rankings of wet peak data for established tread compounds. Wet slide traction data is much more sensitive, however, and apparatus parameters must be carefully controlled for the apparatus to duplicate known rankings for slide traction. The load on the sample and the speed of rotation of the sample greatly affect the rankings.

Since anti-lock brakes are being used on cars in increasing numbers, the peak torque and slide curve separately are less important than they were in the past since an anti-lock brake is designed to release as it approaches the peak torque, and maintain some level of traction above the slide curve.

The apparatus can be used to obtain conventional traction curves, or using the computer control of the apparatus, it is possible to run sample tests under programs that simulate anti-lock brakes, further optimizing the data obtained.

The lab traction coefficient M is calculated using the relationship $$M = \frac{3T(r_o^2 - r_i^2)}{2F_n(r_o^3 - r_i^3)}$$

where T is the measured torque, Fn is the applied normal load, $r_o$ is the outer radius of the sample and $r_i$ is the inner radius of the sample. The peak lab traction coefficient is obtained from the transient spike seen in FIG. 5 while the slide lab traction coefficient is calculated from the average value of the torque over one revolution beginning when the specimen has rotated ½ revolution.

The invention is further illustrated with reference to the following Examples.

EXPERIMENTAL

Test surfaces were made from 4142 tool steel and hardened to a Rockwell C hardness of 45. The control surfaces are designated by spacing and depth of a 60 degree mill cutter. A 026×060 control surface specifies that the depth of cut was 0.026 in., and the spacing between cuts was 0.060 in. The 012×040/030×080 surface has a finer 012×040 surface superimposed on a coarser 030×080 surface. Finally, the designation "Radial 4 deg" refers to a control surface where cuts are made every 4 deg at a depth of 0.015 in.

Figure 6A:
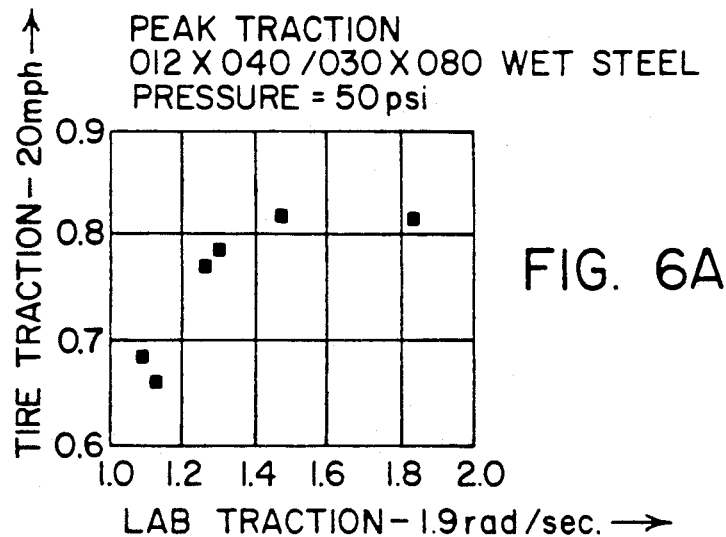
FIGS. 6-8 illustrate data obtained using a horizontally oriented traction device.
Figure 6B:
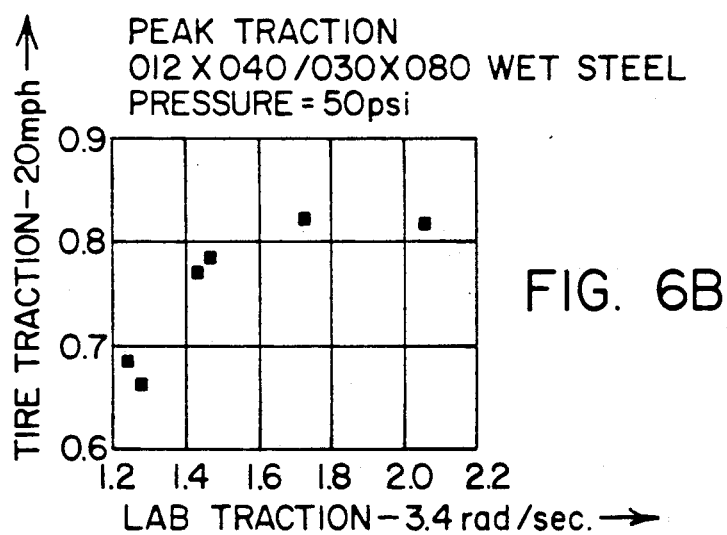
Figure 6C:
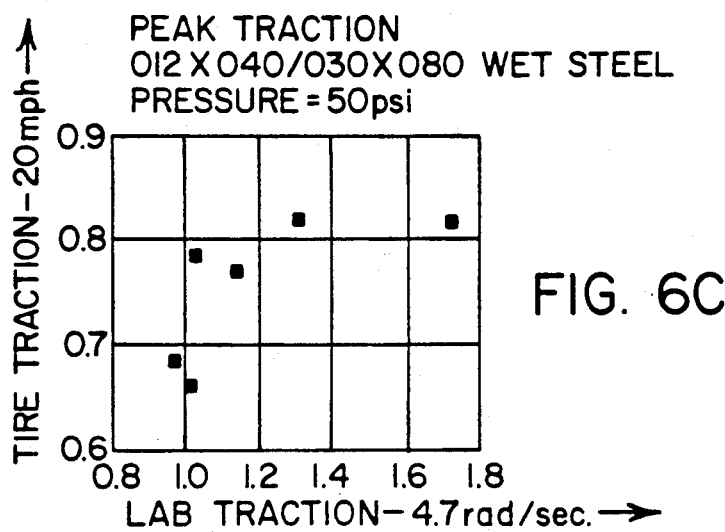
Figure 7A:
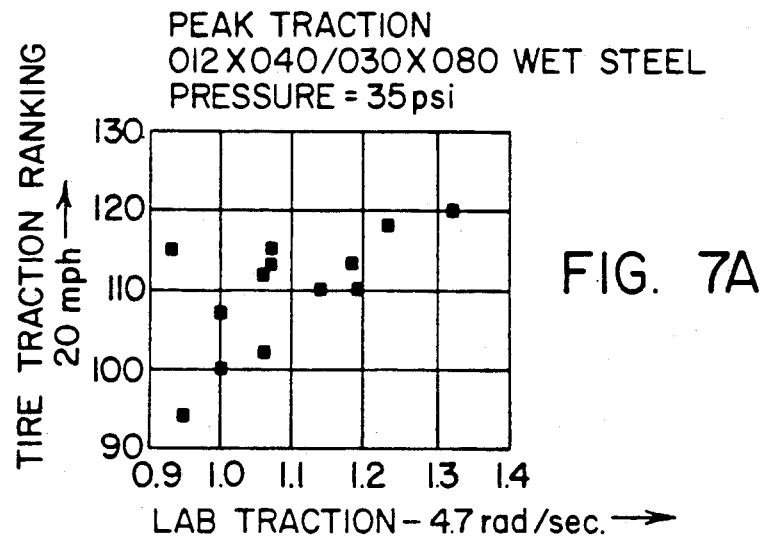
Figure 7B:
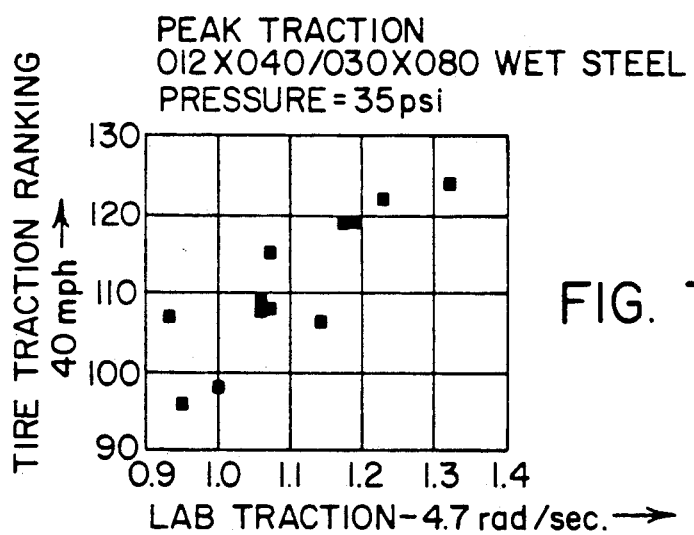
Figure 7C:
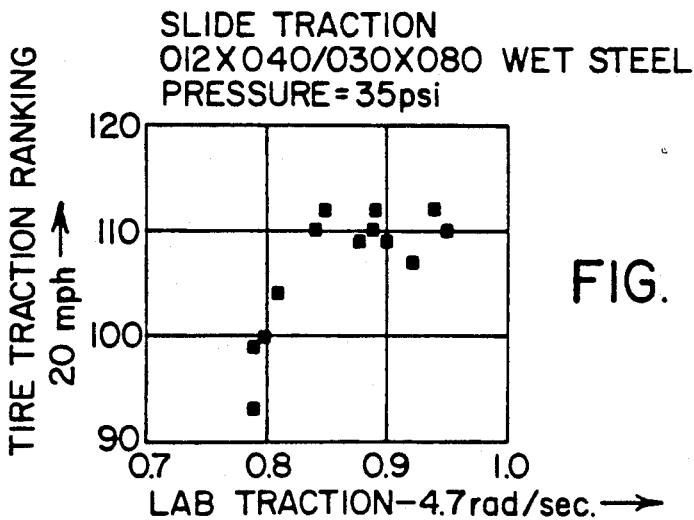
Figure 8A:
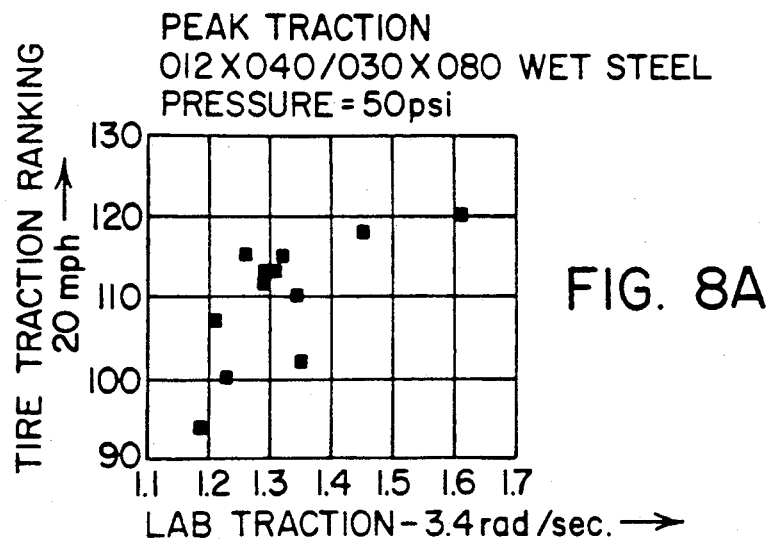
Figure 8B:
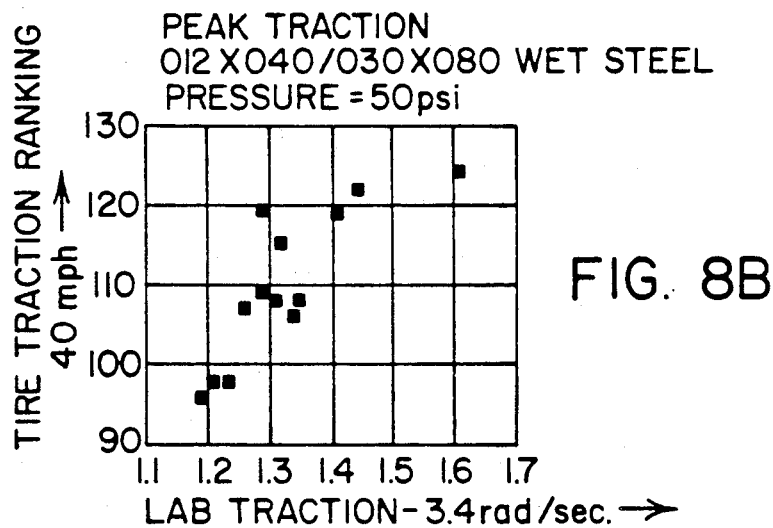
Figure 8C:
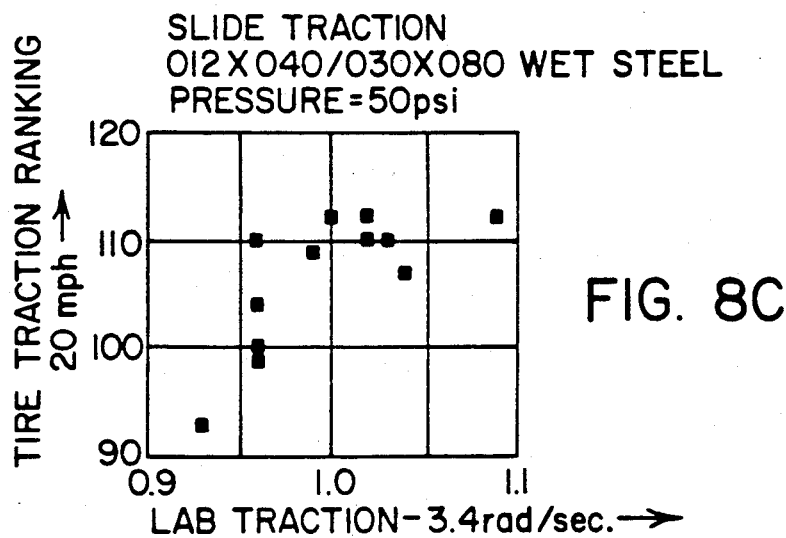

The data illustrated in FIGS. 6-8 was obtained using a traction device put together from available laboratory equipment in which the sample was held horizontally. The jury-rigged device was useful to prove the concepts described herein. No such data is yet available for the apparatus illustrated herein.

EXAMPLE 1

Annular test samples were cured in a cavity mold. Surface preparation of the samples consisted of eight revolutions at 50 psi applied pressure and 10 rpm angular velocity on a 120 grit aluminum oxide abrasive surface. The sample was then cleaned with alcohol. All samples were mounted, and their surfaces were prepared prior to testing.

A strict test procedure was adhered to throughout all the testing and consisted of wetting the test surface and sample with water and running the sample against the test surface at test speed and load for eight revolutions, loading and unloading every two revolutions. This served as a break-in immediately prior to testing. The sample was then cleaned with alcohol, reloaded, and tested.

Rubber is much softer than road surfaces and the minor differences in the hardness of road surfaces (as between concrete and asphalt, for example) are not considered in lab testing at this time. The test procedure consisted of loading the sample in the quick-change fixture and then applying the test load. Within 0.025 seconds of reaching the test load, the sample was rotated for 2 revolutions. The time of 0.025 seconds was chosen because it is the approximate amount of time a lug is in contact with the road surface when a vehicle is travelling 20 mph. Again, this is an important factor as is the asperity/speed relationship, since letting the sample sit too long before rotating will cause greater deformation of the rubber and, a higher coefficient of traction. Once the sample had completed 2 revolutions, the load was removed from the sample, the test sample was unloaded from the tester, and it was cleaned with alcohol before the next test was run.

This procedure was done four consecutive times for each sample, rotating with the starting position of the sample 90° each time. Changing the starting position was one method of compensating for the effects of any system nonconcentricity and nonparallelism. Two samples of each compound were tested for a total of eight tests per individual compound. All the data collected for each compound were used in calculating the lab traction coefficients. That is, there was no correction made for extraneous data points or to reduce the scatter of the data.

1. Effect of Test Surface

The first tests were run on a variety of surfaces to assess the effect of the control surface on the lab traction coefficient. Tests were run at 50 psi contact pressure and a rotational speed of 3.4 rad/sec. Peak lab traction coefficients were plotted against the actual tire traction coefficients obtained at 20 mph on wet asphalt. Six compounds tested were generally separated into three to four groups and the test control surface influenced the magnitude and spread of the lab traction coefficients.

All ingredients in the test compounds described below are in phr (parts per hundred parts rubber).

| TREAD COMPOUND FORMULATIONS | | | | | | |
|---|---|---|---|---|---|---|
| Compound | 1 | 2 | 3 | 4 | 5 | 6 |
| Natural Rubber | 0 | 10 | 50 | 30 | 30 | 30 |
| Solution SBR | 0 | 0 | 50 | 70 | 70 | 70 |
| Emulsion SBR | 100 | 90 | 0 | 0 | 0 | 0 |
| Carbon Black | 55 | 45 | 40 | 45 | 30 | 20 |
| Silica | 10 | 10 | 15 | 10 | 10 | 10 |
| Processing Aids | 22.5 | 18.5 | 10.17 | 18.67 | 12.67 | 8.67 |
| Antidegradents | 2.97 | 2.97 | 2.97 | 2.97 | 2.97 | 2.97 |
| Sulfur – Accelerators | 3.0 | 2.7 | 2.5 | 2.6 | 2.6 | 2.6 |
| Zinc Oxide | 3.5 | 3.5 | 3.5 | 3.5 | 3.5 | 3.5 |

It was found that the lab traction coefficients were a minimum of about 35% higher than the tire traction coefficients. Control surface asperity size and distribution appeared to have a nonlinear effect on the peak lab traction coefficient. Surfaces with small asperities and high frequency such as the 012×040/030×080 surface tended to accentuate the differences separated the compounds into four groups and yielded the highest peak lab traction values.

TABLE 1

| Lab Traction Results for Example 1 Compounds | | | | | | |
|---|---|---|---|---|---|---|
| PEAK | | | SLIDE | | | |
| CMPD | COEF | | CMPD | COEF | | |
| 1 | 2.06 A | | 1 | 1.15 A | | |
| 2 | 1.73 | B | 2 | 1.13 A | B | |
| 3 | 1.47 | C | 3 | 1.07 | B | C |
| 4 | 1.44 | C | 4 | 1.05 | | C |
| 6 | 1.28 | D | 5 | 0.97 | | D |
| 5 | 1.24 | D | 6 | 0.91 | | D |

Tests performed at 50 psi contact pressure and 3.4 rad/sec on a wet 012×404/030×080 steel surface.
NOTE: Coefficients with the same letter are not significantly different.

The grouping of the compounds varied with the control surface, but in general could be considered to fall into three groups with Compounds 1 and 2 having the highest traction followed by 4 and 3, with 6 and 5 having the lowest traction. This grouping agrees very well with the ranking and separation attained by tire traction tests as shown in Table 2.

TABLE 2

| GM Tire Traction Results for Compounds of Example 1 | | | |
|---|---|---|---|
| CMPD | COEF | CMPD | COEF |
| PEAK - 20 mph WET ASPHALT | | SLIDE - 20 mph WET ASPHALT | |
| 2 | .8186 | 1 | .5437 |
| 1 | .8165 | 2 | .5008 |
| 3 | .7856 | 4 | .4827 |
| 4 | .7707 | 3 | .4667 |
| 5 | .6847 | 5 | .4398 |
| 6 | .6613 | 6 | .4302 |
| PEAK - 40 mph WET ASPHALT | | SLIDE - 40 mph WET ASPHALT | |
| 2 | .7606 | 1 | .4098 |
| 1 | .7557 | 2 | .3928 |
| 3 | .6920 | 4 | .3832 |
| 4 | .6817 | 3 | .3723 |
| 6 | .5877 | 5 | .3562 |
| 5 | .5807 | 6 | .3476 |

The test surface giving best results had 0.016 in. square asperities, superimposed on 0.046 in., square asperities, with their respective depths being 0.012" and 0.030". It is noted, however, that this surface was used to simulate traction testing on asphalt at Goodyear's San Angelo testing facility, and that the surface must be matched to the contact pressure and rotational speed of the test. It is the deformation and rate of deformation of tread lugs that must be simulated in the lab environment in order to obtain a meaningful correlation. The uniqueness of the machined test surface aspect of this invention is that any road surface can be simulated and, therefore, the traction on any of these road surfaces can be predicted. For most roads of asphalt and concrete, test surface asperities would range from 0–0.250" wide and 0–0.250" deep.

2. Effect of Speed

The effect of rotational speed on the peak lab traction coefficient was investigated by varying the speed from 1.9 rad/sec to 4.7 rad/sec. LTT speed is expressed in terms of angular speed rather than linear speed to avoid comparison with vehicle speed. The important parameter for peak traction is the rate of deformation of the tread rubber and, therefore, it is not necessary to match the linear speed of the LTT with the vehicle speed of the GM Traction Test. Plots of lab versus tire traction coefficients for the above speeds are shown in FIG. 6A, 6B and 6C. These tests were performed on a wet 012×040/030×080 steel control surface at 50 psi nominal contact pressure. The best separation or distinction of compound properties, and correlation with tire traction coefficients, was obtained at 3.4 rad/sec. Lower speeds ranked the compounds correctly but did not statistically separate the compound properties as well. Raising the speed to about 3.4 rad/sec had a greater effect on the compound rankings and scatter than did lowering the speed. Results obtained at 4.7 rad/sec were worse than those obtained at any other speed.

3. Slide Lab Traction Coefficient

The peak traction coefficient is of primary interest since it determines the point where traction is lost, and it will become increasingly important as anti-lock brake systems become more prevalent. Nevertheless, the ability to predict the slide traction coefficient was also investigated. The slide traction coefficient was much more sensitive to the choice of control surface and rotational speed than the peak coefficient and was much more difficult to predict. In contrast to the peak coefficient where variations in surface and speed affected the separability of the compounds more than the absolute ranking, the slide coefficient rankings could be drastically changed by small changes in the surface roughness (e.g. asperity frequency) and rotational speed. The only control surface tested that produced a correlation between lab and tire slide coefficients was the 012 040/030 080 steel surface. The best correlation obtained was at 3.4 rad/sec. It was also noted that the lab slide traction had considerably lower values than the lab peak coefficient. The lab slide coefficients were not as low as the tire slide coefficients, but the ratio of slide-to-peak for both the tire and lab tests was comparable and approximately 30–40% for the test conditions.

4. Effect of Contact Pressure

The average contact pressure in the footprint of a passenger tire has been experimentally determined to be approximately 50 psi in most situations. This value was the desired choice for lab testing. However, tests were performed at three pressures: 35, 50 and 75 psi, to assess the effect of pressure. Good correlation of peak lab and tire traction coefficients was obtained at both 35 and 50 psi. An applied pressure of 50 psi yielded slightly better results for slide traction compared to 35 psi, when high modulus compounds were tested. Results obtained at 75 psi had very poor correlation with tire traction results.

EXAMPLE 2

An additional thirteen compounds were tested using the Laboratory Traction Test. Differences between these compounds were not as pronounced as the differences between the compounds of Example 1, and this was attributed to the narrower range of compound physicals.

In the formulations below, NR indicates natural rubber, acc is short for accelerators, and S-SBR (1–7) represents seven different solution styrene butadiene rubbers. SIBR represents styrene isoprene butadiene rubber. CB is short for carbon black. All ingredients are listed in terms of phr.

| | TREAD COMPOUND FORMULATIONS | | | | | | | | | | | | |
|---|---|---|---|---|---|---|---|---|---|---|---|---|---|
| Compound | 7 | 8* | 9* | 10 | 11 | 12 | 13 | 14 | 15 | 16 | 17 | 18 | 19 |
| NR | 30 | 50 | 50 | 85 | 50 | 50 | 50 | 50 | 40 | 40 | 50 | 50 | 75 |
| S-SBR1 | | | | | 50 | | | | | | | | |
| S-SBR-2 | | | | | | | | | | 50 | 50 | | 50 |
| S-SBR-3 | | | | | | | | | | | 25 | | |
| S-SBR-4 | | | | | | | | | | | 25 | | |
| S-SBR-5 | | | | | | | | | 50 | | | | |
| S-SBR-6 | 70 | 50 | 50 | | | | | | | | | | |
| S-SBR-7 | | | | | | 50 | | | | | | | |
| Nitrile Rubber | | | | | | | | | | 10 | | | |
| Polyisoprene | | | | | | | | | | | | | 25 |
| SIBR | | | | | | | 50 | | | | | | |
| Silica | 17 | 17 | 17 | 15 | 17 | 17 | 17 | 17 | 17 | 17 | 17 | 17 | 17 |
| CB-1 | | | | 40 | 43 | | 43 | | | | | | |
| CB-2 | 38 | 38 | 38 | | | 38 | | 50 | 38 | 38 | 38 | 38 | 38 |
| Processing Aids | 7 | 7 | 7 | 3.5 | 7 | 7 | 7 | 7 | 7 | 7 | 7 | 7 | 7 |
| Anti-Degradants | 3.37 | 3.37 | 3.37 | 2.97 | 3.37 | 3.37 | 3.37 | 3.37 | 3.37 | 3.37 | 3.37 | 3.37 | 2.97 |
| Sulfur + Acc | 2.65 | 2.57 | 2.57 | 2.5 | 2.82 | 2.82 | 2.77 | 2.82 | 2.77 | 2.77 | 2.82 | 2.82 | 2.37 |
| Zno | 3.5 | 3.5 | 3.5 | 3.5 | 3.5 | 3.5 | 3.5 | 3.5 | 3.5 | 3.5 | 3.5 | 3.5 | 3.5 |
| Isoprene Acrylonitrile | | | | 15 | | | | | 10 | | | | |

*8 and 9 contain the same ingredients but were mixed differently

Compounds 7 and 8 were found to have the highest peak lab traction coefficients while Compounds 16, 18 and 17 had the lowest peak lab traction coefficients.

TABLE 3

Lab Traction Results of Example 2 Compounds.*

| PEAK | | | | | SLIDE | | | | | |
|---|---|---|---|---|---|---|---|---|---|---|
| CMPD | COEF | | | | | CMPD | COEF | | | |
| 7 | 1.32 | A | | | | 8 | 0.95 | A | | |
| 8 | 1.23 | A | B | | | 7 | 0.94 | A | | |
| 9 | 1.19 | | B | | | 9 | 0.92 | | B | |
| 10 | 1.18 | | B | | | 19 | 0.90 | | | C |
| 11 | 1.14 | | B | C | | 10 | 0.89 | | | C |
| 12 | 1.07 | | | C | D | 13 | 0.89 | | | C |
| 13 | 1.07 | | | C | D | 11 | 0.88 | | | C |
| 14 | 1.06 | | | C | D | 12 | 0.85 | | | D |
| 15 | 1.06 | | | C | D | 14 | 0.84 | | | D |
| 16 | 1.00 | | | | D E | 17 | 0.81 | | | E |

TABLE 3-continued

Lab Traction Results of Example 2 Compounds *

| PEAK | | | | | SLIDE | | |
|---|---|---|---|---|---|---|---|
| CMPD | COEF | | | CMPD | COEF | | |
| 17 | 1.00 | D | E | 15 | 0.80 | E | F |
| 18 | 0.95 | | E | 18 | 0.79 | E | F |
| 19 | 0.93 | | E | 16 | 0.79 | | F |

*Tests performed at 35 psi contact pressure and 4.7 rad/sec on a wet .012 × .040/.030 × .080 steel surface.

NOTE: Coefficients with the same letter are not significantly different.

FIGS. 7 and 8 show the results for two test conditions: 35 psi/4.7 rad/sec and also 50 psi/3.4 rad/sec. It is noted that the data point for compound 19 appears to be anomalous. Extraneous physical test data of the lab samples of Compound 19 were also found, and it appears as though there may have been a discrepancy between the lab compound and the tire compound. Nevertheless, the ranking of the compounds was promising with good correspondence between high peak traction values in the lab and on the tire and between low peak traction in the lab and on the tire.

TABLE 4

GM Tire Traction Results for Example 2 Compounds

| CMPD | RANK | LSD | CMPD | RANK | LSD |
|---|---|---|---|---|---|
| PEAK - 20 mph WET ASPHALT | | | SLIDE - 20 mph WET ASPHALT | | |
| 7 | 120 | 3.2 | 7 | 112 | 3.1 |
| 8 | 118 | 2.9 | 12 | 112 | 4.2 |
| 19 | 115 | 2.5 | 13 | 112 | 2.3 |
| 12 | 115 | 4.3 | 8 | 110 | 2.6 |
| 10 | 113 | 2.9 | 14 | 110 | 2.7 |
| 13 | 113 | 3.1 | 10 | 110 | 2.8 |
| 14 | 112 | 3.3 | 19 | 109 | 2.9 |
| 9 | 110 | 5.0 | 11 | 109 | 1.5 |
| 11 | 110 | 2.3 | 9 | 107 | 3.8 |
| 17 | 107 | 3.0 | 17 | 104 | 3.3 |
| 15 | 102 | 3.2 | 15 | 100 | 2.7 |
| 16 | 100 | 3.0 | 16 | 99 | 2.4 |
| 18 | 94 | 2.6 | 18 | 93 | 2.8 |
| PEAK - 40 mph WET ASPHALT | | | SLIDE - 40 mph WET ASPHALT | | |
| 7 | 124 | 3.9 | 13 | 111 | 2.8 |
| 8 | 122 | 4.0 | 7 | 110 | 2.9 |
| 9 | 119 | 4.2 | 12 | 110 | 3.4 |
| 10 | 119 | 5.1 | 10 | 109 | 3.2 |
| 12 | 115 | 4.9 | 11 | 109 | 2.9 |
| 14 | 109 | 3.6 | 14 | 108 | 2.5 |
| 15 | 108 | 4.5 | 8 | 107 | 2.6 |
| 13 | 108 | 2.9 | 9 | 107 | 3.1 |
| 19 | 107 | 2.7 | 19 | 105 | 2.0 |
| 11 | 106 | 2.6 | 17 | 104 | 1.5 |
| 17 | 98 | 2.4 | 16 | 104 | 1.8 |
| 16 | 98 | 2.7 | 15 | 103 | 2.8 |
| 18 | 96 | 2.8 | 18 | 96 | 2.4 |

It was also interesting to note that slightly greater separation of the compound properties was found at 35 psi/4.7 rad/sec than at 50 psi/3.4 rad/sec and that correlation of peak lab traction with peak tire traction at 40 mph was better than with peak tire traction at 20 mph. Again, correlation of slide lab traction and slide tire traction was not as good as that obtained for peak traction. Slightly better correlation was obtained using the 50 psi/3.4 rad/sec condition. It should be pointed out that there was poor separation of the slide tire traction results as shown in Table 4. Therefore, the lab results are not surprising.

EXAMPLE 3

The compounds tested on the lab prototype in Example 1, were tested again using the machine having a vertical sample holder as described herein, using the same procedures described in Example 1 with the following results.

TABLE 5

LAB TRACTION TEST - November 26, 1990
WET PEAK TRACTION
.012 × .040/.030 × .080 STEEL
70 DEG F. - 50 psi - 30 rpm
ANALYSIS OF VARIANCE PROCEDURE
WALLER-DUNCAN K-RATIO T TEST FOR VARIABLE: UPEAK
NOTE: THIS TEST MINIMIZES THE BAYES RISK UNDER ADDITIVE LOSS AND CERTAIN OTHER ASSUMPTIONS.
KRATIO = 100  DF = 42  MSE = .0038687  F = 66.4588
CRITICAL VALUE OF T = 1.80
MINIMUM SIGNIFICANT DIFFERENCE = .05597
MEANS WITH THE SAME LETTER
ARE NOT SIGNIFICANTLY DIFFERENT

| WALLER GROUPING | MEAN | N | COMP |
|---|---|---|---|
| A | 1.53796 | 8 | 1 |
| B | 1.47635 | 8 | 2 |
| C | 1.33615 | 8 | 3 |
| C | | | |
| C | 1.32978 | 8 | 4 |
| D | 1.11948 | 8 | 6 |
| D | | | |
| D | 1.10036 | 8 | 5 |

It is noted that the ratings of the compounds are the same as those seen in Example 1 although the mean torque measurement is different.

EXAMPLE 4

An additional feature of the Lab Traction Tester is that its servo motors can be programmed for very precise motion control and sequencing of the motors. This allows a test procedure to be automated thereby precisely controlling the time interval between break-in and testing a given sample. Given the viscoelastic nature of tread compounds, controlling the time variability during testing greatly enhances the accuracy and reproducibility of the test.

A test procedure incorporating the programming capabilities of the tester was developed and involved the cyclic loading and rotating of the sample. The test sequence includes the loading of the sample at a given linear rate, rotation of the sample at a prescribed angular speed immediately following the loading, unloading of the sample following termination of rotation, and then repetition of this sequence four more times. The first lab traction curve obtained from this procedure is used for break-in and is therefore discarded. The lab traction coefficient is then obtained from the average of the next four curves. The initial peak is higher than the second and third, and the second and third peaks are nearly identical. The fourth and fifth peaks are also nearly identical to the second and third peaks. The benefit of this cyclic loading procedure is that the rate and frequency of loading can be precisely matched to that of a tread lug on a tire travelling at a given speed and the rotational speed can be set to match the rate of deformation (shear rate) that a tread lug is subject to once it is in the footprint.

The same compounds and same machine used in Example 1 were used for further testing using a cyclic loading procedure. In the cyclic loading procedure the machine is programmed to load and test and unload the sample 5 times in about a 5 second period. The data obtained from the first loading is discarded and the mean data from the other four tests are retained and averaged. Cyclic loading gives more consistent results as illustrated by the low mean difference shown by the data.

TABLE 6

LAB TRACTION TEST
WET PEAK TRACTION
012 - 040/030 - 080 STEEL
70 DEG F. - 50 psi - rpm - CYCLIC LOADING
ANALYSIS OF VARIANCE PROCEDURE
WALLER-DUNCAN K-RATIO T TEST FOR VARIABLE:
UPEAK
NOTE: THIS TEST MINIMIZES THE
BAYES RISK UNDER ADDITIVE
LOSS AND CERTAIN OTHER ASSUMPTIONS
KRATIO = 100 DF = 42 MSE = .0011019 F = 57.2526
CRITICAL VALUE OF T = 1.80
MINIMUM SIGNIFICANT DIFFERENCE = .02991
MEANS WITH THE SAME LETTER ARE
NOT SIGNIFICANTLY DIFFERENT

| WALLER GROUPING | MEAN | N | COMP |
|---|---|---|---|
| A | 1.25225 | 8 | 1 |
| B | 1.19383 | 8 | 2 |
| B | | | |
| B | 1.18002 | 8 | 3 |
| C | 1.12479 | 8 | 4 |
| D | 1.04301 | 8 | 5 |
| D | | | |
| D | 1.02707 | 8 | 6 |

Since traction is dependent on speed, load and traction surface, a compound that shows good traction on a passenger tire (tested at 20 mph, 20 psi) may not show good traction on a racing tire (tested at 40 mph, 10 psi), and vice versa. This illustrates the specificity of the tests and the specificity of the compounds that can be used. Also, if a specific formulation fails for it intended purpose, further testing may provide a valuable other use for the formulation.

While specific embodiments of the invention have been illustrated and described, those skilled in the art will recognize that the invention may be variously modified and practiced without departing from the spirit of the invention. The invention is limited only by the following claims.

I claim:

1. A method of predicting tire traction characteristics of tread compounds comprising the steps of:
   (a) preparing a sample of tread compound in a form suitable for traction testing;
   (b) placing said sample in a testing apparatus opposite a testing surface, said apparatus being capable of causing a rotating relationship between said sample and test surface and measuring the torque therebetween;
   (c) contacting said sample with said test surface and initiating a rotating relationship;
   (d) measuring the peak torque and establishing a torque v. time curve for said sample (slide traction); and
   (e) correlating said torque v. time curve with established curves for desired traction characteristics.

2. The method of claim 1 comprising the further step of preparing said testing surface to have characteristics that resemble a particular road surface.

3. The method of claim 1 comprising the further steps of:
   (a) providing means for controlling the pressure, speed and temperature between said sample and said test surface;
   (b) controlling the pressure of the contact between said sample and said test surface;
   (c) controlling the relative speed of rotation of said sample and said test surface; and
   (d) controlling the temperature of said sample and said test surface.

4. The method of claim 1 further comprising the step of preparing said sample to have an annular shape.

5. The method of claim 1 comprising the further step of making said test surface from a non-corrosive, durable material.

6. The method of claim 5 which comprises the further step of milling said test surface to provide asperities of varying sizes to match the properties of asperities in a given road surface.

7. The method of claim 1 which further comprises the step of orienting said testing apparatus vertically such that said sample and said test surface may be disposed horizontally, one above the other.

8. The method of claim 7 which comprises the step of disposing said test surface below said sample, and adapting said testing apparatus to hold a specified depth of water over said test surface for wet testing of said sample.

9. An apparatus for predicting tire traction characteristics of tread compounds comprising:
   (a) a frame comprising a horizontally disposed base and a horizontally disposed top, each having an upward side and a downward side, said top and base being connected by vertically disposed guide rails;
   (b) a motor associated with said top with a driveshaft thereof oriented vertically downward on the downward side of said top;
   (c) a sample mount attached to said drive shaft;
   (d) a loading cylinder disposed on the upward side of said base;
   (e) a movable plate having an upper surface contacting said loading cylinder upwardly of said loading cylinder, said movable plate engaging said guide rails;
   (f) a load cell on said upper surface of said movable plate in vertical alignment with said sample mount; and
   (g) a test cell comprising means for holding a fluid associated with said load cell, the base of said cylinder comprising a test surface, said test surface being designed to demonstrate the properties of a road surface,
   wherein said loading cylinder is adapted to move said movable plate on said vertical guide rails to bring said test cell into contact with said sample mount.

10. The apparatus of claim 9 further comprising a chamber attached to said movable plate and movably engaging a sealing means associated with said top, said chamber providing means for controlling the environment around said sample mount.

11. The apparatus of claim 9 wherein said sample mount is adapted to receive a preformed sample in a snap-in relationship.

12. The apparatus of claim 9 which further comprises means for precisely controlling the speed of said motor.

13. The apparatus of claim 9 which further comprises means for precisely controlling pressure provided by said loading cylinder for bringing a sample in said sample mount into contact with said test surface.

* * * * *